United States Patent
Griffiths et al.

(10) Patent No.: US 6,913,754 B1
(45) Date of Patent: Jul. 5, 2005

(54) RENIBACTERIUM SALMONINARUM VACCINE

(75) Inventors: Steven Gareth Griffiths, Fredericton (CA); Kira Salonius, Cornwall (CA)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/634,681

(22) Filed: Aug. 5, 2003

Related U.S. Application Data

(63) Continuation of application No. 09/355,474, filed as application No. PCT/GB98/00256 on Jan. 28, 1998, now Pat. No. 6,627,203.

(30) Foreign Application Priority Data

Jan. 30, 1997 (GB) ............................................. 9701897

(51) Int. Cl.$^7$ .............................................. A61K 39/02
(52) U.S. Cl. ............................. 424/234.1; 424/184.1; 435/243; 435/252.1
(58) Field of Search .......................... 424/184.1, 234.1; 435/243, 252.1

(56) References Cited

FOREIGN PATENT DOCUMENTS

WO    WO 96/11717    4/1996

OTHER PUBLICATIONS

Koch et al., "16S rDNA Studied on Membranes of Arthrobacter and Micrococcus: An Aid for their Future Taxonomic Restructuring", FEMS Microbiology Letters, vol. 123, pp. 167–171, (1994).

S.G. Griffiths et al., "Reduction of Renibacterium Culture Activity in Atlantic Salmon Following Vaccination with Avirulent Strains", Fish & Shelfish Immunology, vol. 8, pp. 607–619, (1998).

Mori et al. Bull. JPN Soc Sci Fish, 46(6): 717–722, (1980) Abstract only.

Karaskiewicz, J. Pr. Inst. Naft. Poland, V20505/IB, 1974, p. 67, Abstract only.

*Primary Examiner*—Jennifer E. Graser
(74) *Attorney, Agent, or Firm*—David L. Marks

(57) ABSTRACT

The invention provides and immune stimulating agent or vaccine directed to *Renibacterium salmoninarum* comprising a live non-virulent culture of an *Arthrobacter* strain based on, derived from or substantially homologous with strain RSxII as deposited as ATCC 55921. The culture may be presented in lyophilized form with a sterile diluent.

12 Claims, No Drawings

RENIBACTERIUM SALMONINARUM VACCINE

The application is a continuation of U.S. patent application Ser. No. 09/355,474, filed Apr. 5, 2000, now U.S. Pat. No. 6,627,203, which is a National Stage of International Patent Application PCT/GB98/00256 filed on Jan. 28, 1998.

Protection of farmed fish against bacterial disease caused by *Renibacterium salmoninarum* by the use of a live strain of *Arthrobacter* spp. The working designation of this species, RSxll, is used through this document.

This invention relates to the protection of farmed fish against disease caused by the bacterial species *Renibacterium salmoninarum*. This disease colloquially named bacterial kidney disease or BKD from some aspects of it pathology, is one of the most economically serious diseases in salmonoid culture. Conservative estimates suggest that losses on the west coast of Canada exceed 20 million dollars annually. Similar problems have occurred in Chile and the Pacific coast of the USA. The farming of some species, such as Chinook and Coho salmon, has become economically unsustainable in these areas due to this disease. In cooler waters such as Eastern Canada and Northern Europe, the disease is characterized by less severe symptoms and gives rise generally to chronic infections. The consequent poor growth performance and increased susceptibility to concurrent disease cause a high economic loss in these industries also.

A number of the standard methods for the production of effective vaccines have been used in efforts to provide protection against *Renibacterium salmoninarum*. Generally these have proved to be ineffective and, where successes have been reported by particular groups, these have provided unreplicable in the hands of others. Such methods have employed killed cells and cell fragments with or without adjuvants.

The key factor in this lack of success is probably the ability of *Renibacterium* to survive and possibly multiply within the macrophages of the host fish. In this situation it is protected from the main immune systems of the host. Constant "leakage" of cells from the macrophages causes a low-level persistent infection which constantly challenges the fish immune system. Controlling this under normal conditions lowers the fitness of the animal and, if a further environmental or disease stress occurs, the Renibacterial cells may initiate a more damaging infection. Sometime during this process a full immune response may be mounted to the disease but this proves to be ineffective since large quantities of a 57 kilodalton protein are produced by *Renibacterium* which induces the production of large quantities of antibodies which are not protective. The "preoccupation" of the humoral immune system with this protein prevents an effective response being made to other components of the bacteria which might confer protection. The p57 protein therefore acts as an effective decoy.

The most successful of the approaches to vaccination against *Renibacterium* have all used Freund's Complete Adjuvant (FCA). This aids in the effective presentation of antigens to the T-cells in the normal way but is also, independently, a powerful stimulator of the non-specific cellular immune responses. FCA contains cell wall fragments obtained from species of *Corynebacterium*. The taxonomic relationships between bacteria recognised under this and associated genera are not clear and Renibacteria were originally classified as Corynebacteria. Some strains of Renibacteria also have powerful stimulators of non-specific immunity on their cell surfaces further suggesting a close taxonomic relationship. The closely relates genus *Arthrobacter* also contains species which have similarly reactive groups on their surface capable of stimulating non-specific immunity. Cells of this genus, not capable of causing disease but containing such groups on their surface and probably also antigens in common with *Renibacterium*, might reasonably be expected to stimulate powerful specific and non-specific immunity conferring protection against disease. The use of such *Arthrobacter* as live cells, capable of surviving inside macrophages, would prolong the stimulation and extend protection for a commercially acceptable period of time.

It is an object of the present invention to provide an improved vaccine against *Renibacterium salmonarium*.

Accordingly the present invention provides an immune stimulating agent or vaccine comprising a live, non-virulent culture of an *Arthrobacter* strain.

The invention further provides a vaccine directed to *Renibacterium salmoninarium* comprising a live non virulent culture of an *Arthrobacter* strain.

Preferably, the *Arthrobacter* strain is based on or is derived from strain RSxll, as deposited under Accession No ATCC 55921 with the American Type Culture Collection, 10801 University Boulevard, Manassas, Va. 20109, on 20 Dec. 1996.

Suitably the strain is characterised by a partial 16s DNA sequence derived from the following:

GAGTTTGATCCTGGCTCAGGAT-
GAACGCTGGCGGCGTGCTTAACACATG-
CAAGTCG
AACGATGAACCTGTGCTTGCACGGGG-
GATTAGTGGCGAACGGGTGAGTAACACGT
GAGTAACCTGCCCTTGACTTCGG-
GATAAGCCTGG-
GAAACTGGGTCTAATACTGGAT
ACGACCTCTCATCGCATGGTGTC-
CCCCTGGAAAGTTTTTGCGGTTTTG-
GATGGACT
CGCGGCCTATCAGCTTGTTGGTGAGG-
TAATGGCTCACCAAGGCGACGACGGGTAG
CCGGCCTGAGAGGGTGACCGGCCA-
CACTGGGACTGAGACACGGCCCAGACTCCTA
CGGGAGGCAGCAGTGGGGAATATTGCA-
CAATGGGCGAAAGCCTGATGCAGCGACG
CCGCGTGAGGGACGACGGCCTTCGGGT-
TGTAAACCTCTTTCAGTAGGGAACAAGG
CATCATTTTTGTGGTGTTGAGGGTACT-
TGCAGAAGAAGCACCGGCTAACTACGTGC
CAGGCGCCGCGGTAATACGTAGGGTG-
CAAGCGTTATCCGGAATTATTGGGCGTAAA
GAGCTCGTAGGCG-
GTTTGTCGCGTCTTTCGTGAAAGTC-
CGGGGCTCAACTCCGGAT
CTTCGGTGGGTACGGGCAGACTAGAGT-
GATGTAGGGGAGACTGGAATTCCTGGTG
TAGCGGTGGAATGCGCAGATATCAGGAG-
GAACACCGATGGCGAAGGCAGGTCTCT
GGGCATTAACTGACGCTGAGGAGC-
GAAAGCATGGGGAGCGAACAGGATTAGATAC
CCTGGTAGTCC (SEQ ID No: 1)

The invention further provides a pharmaceutical preparation comprising a live, non-virulent culture of an *Arthrobacter* strain.

Suitably the preparation can be used to provide protection against *Renibacterium salmonarium*.

The strain may be characterised by any or all of the following:
1. Positive gram-stain; easily discoloured
2. Non-motile
3. The cells, in the log phase of growth, are 0.8–1.2×1.0–8.0 μm often V-shaped with clubbed ends. As growth proceeds into stationary phase the rods segment into small cocci, 0.6–1.0 μm in diameter.
4. The enzymatic reactions used in diagnosis are as follows where + indicates positive, − indicates negative and (+) indicates a weak positive:

| | | |
|---|---|---|
| i) | Alkaline phosphatase | + |
| ii) | Butyrate esterase ($C_4$) | + |
| iii) | Caprylate esterase ($C_8$) | + |
| iv) | Myristate lipase ($C_{14}$) | − |
| v) | Leucine arylamidase | + |
| vi) | Valine arylamidase | (+) |
| vii) | Cystine arylamidase | − |
| Viii) | Trypsin | + |
| ix) | Chymostrypsin | − |
| x) | Acid Phosphatase | + |
| xi) | Phosphoamidase | − |
| xii) | α-Galactosidase | − |
| xiii) | β-Galactosidase | (+) |
| xiv) | β-Glucuronidase | + |
| xv) | α-Glucosidase | + |
| xvi) | β-Glucosidase | − |
| xvii) | N-Acetyl-β-glucosamidase | − |
| xviii) | α-Mannosidase | + |
| xix) | α-Fucosidase | − |

5. Catalase Reaction Positive
6. Oxidase Reaction Negative

Suitably the immune stimulating agent/vaccine is presented as a lyophilised culture. Preferably the vaccine comprises a lyophilised culture in combination with a sterile diluent. The immune stimulating agent/vaccine may be administered by standard methods of vaccination. The invention also comprises the use of an immune stimulating agent/vaccine as hereinbefore defined for the protection of salmonoid fish against *Renibacterium salmoninarum*. The invention is an immune-stimulating agent or vaccine comprised of a live, non-virulent culture of an Arthrobacter species. It would be presented as a lyophilised culture in a ready to use form in a sterile diluent to be administered by any of the standard methods used for the vaccination of fish.

EFFICACY

1. The strain RSxll shares highly specific antigenic determinants with *R. salmoninarum*. Polyclonal antisera raised against *R. salmoninarum* has a high, cross-reactive titre against whole cells of RSxll in an ELISA test system.

2. RSxII has been shown to stimulate the immune system of Atlantic salmon as demonstrated by lymphocyte proliferation assays.

3. It has been repeatedly shown that in direct challenge (in vivo) studies Atlantic salmon infected at 12–14 weeks by peritoneal injection with the pathogen were protected. The size of salmon ranged from 20–100 g in different trials and protection was measured here by the extent of recovery of live bacteria from the anterior kidney, the commonest focus of infection in fish affected by this disease. Using relative percent culture activity (RPCA) as an index protection ranged from 57–87% in trails where the level of infection in non-vaccinated fish was always greater than 80%. RPCA is derived as follows:

$$RPCA = 1 - \frac{[\% \text{ fish cultured positive in vaccinates}]}{[\% \text{ fish cultured positive in controls}]} \times 100$$

4. PCR was used to assess the presence of DNA of the pathogen shed by fish into the holding water as a further, very sensitive measure, of the presence of the pathogen in treated and control populations. Whereas DNA was present in the holding water of non-vaccinated fish it was present as a trace or absent from that of the vaccinates. The levels correlated well with the levels obtained by the culture technique validating that method. The vaccine disclosed herein protects fish against *Renibacterium salmoninarum* to a greater extent than consistently achieved previously by any other formulation or method.

It is protective rather than a treatment and therefore reduces the chances of an infection becoming established, reduces or eliminates the requirement for drug therapy and promotes growth by retaining the fish at a higher level of fitness. Unlike drug treatment it poses no risk to the environment since the invention comprises an organism isolated from the natural environment and which has been shown to be non-pathogenic for other animal species. It can be administered concurrently with other vaccines within the standard routine of farm husbandry.

What is claimed is:

1. A method of inducing a immune response against *Renibacterium salmoninarum* in fish comprising administering an effective immunizing dose of *Arthrobacter* strain RSxll to said fish.

2. The method of claim 1 wherein said immunizing dose contains an adjuvant.

3. The method of claim 1 wherein said *Arthrobacter* strain RSxll has ATCC Deposit Accession No ATCC 55921.

4. The method of claim 3 wherein said immunizing dose contains an adjuvant.

5. A method of immunizing a fish to a disease caused by *Renibacterium salmoninarum* comprising administering an effective immunizing dose of *Arthrobacter* strain RSxll to said fish.

6. The method of claim 5 wherein said immunizing dose contains an adjuvant.

7. The method of claim 5 wherein said *Arthrobacter* strain RSxll has ATCC Deposit Accession No ATCC 55921.

8. The method of claim 7 wherein said immunizing dose contains an adjuvant.

9. A method for preventing the occurrence of bacterial kidney disease in fish comprising administering an effective immunizing amount of *Arthrobacter* strain RSxll to said fish.

10. The method of claim 9 wherein said immunizing amount contains an adjuvant.

11. The method of claim 9 wherein said *Arthrobacter* strain RSxll has ATCC Deposit Accession No ATCC 55921.

12. The method of claim 11 wherein said immunizing amount contains an adjuvant.

* * * * *

SEQUENCE LISTING

<160> NUMBER OF SEQ ID NOS: 1

<210> SEQ ID NO 1
<211> LENGTH: 787
<212> TYPE: DNA
<213> ORGANISM: Arthrobacter ssp.
<220> FEATURE:
<221> NAME/KEY: gene
<222> LOCATION: (1)...(787)
<223> OTHER INFORMATION: partial 16s DNA sequence

<400> SEQUENCE: 1
gagtttgatc ctggctcagg atgaacgctg gcggcgtgct taacacatgc aagtcgaacg     60
atgaacctgt gcttgcacgg gggattagtg gcgaacgggt gagtaacacg tgagtaacct    120
gcccttgact tcgggataag cctgggaaac tgggtctaat actggatacg acctctcatc    180

-continued

```
gcatggtgtc cccctggaaa gtttttgcgg ttttggatgg actcgcggcc tatcagcttg    240
ttggtgaggt aatggctcac caaggcgacg acgggtagcc ggcctgagag ggtgaccggc    300
cacactggga ctgagacacg gcccagactc ctacgggagg cagcagtggg gaatattgca    360
caatgggcga aagcctgatg cagcgacgcc gcgtgaggga cgacggcctt cgggttgtaa    420
acctctttca gtagggaaca aggcatcatt tttgtggtgt tgagggtact tgcagaagaa    480
gcaccggcta actacgtgcc aggcgccgcg gtaatacgta gggtgcaagc gttatccgga    540
attattgggc gtaaagagct cgtaggcggt ttgtcgcgtc tttcgtgaaa gtccggggct    600
caactccgga tcttcggtgg gtacgggcag actagagtga tgtagggggag actggaattc    660 ctggtgtagc ggtggaatgc gcagatatca ggaggaacac cgatggcgaa ggcaggtctc    720
tgggcattaa ctgacgctga ggagcgaaag catggggagc gaacaggatt agataccctg    780
gtagtcc                                                              787
```